United States Patent [19]
Yaver et al.

[11] Patent Number: 5,705,376
[45] Date of Patent: Jan. 6, 1998

[54] **GENE ENCODING CARBOXYPEPTIDASE OF *ASPERGILLUS NIGER***

[75] Inventors: Debbie Sue Yaver; Sheryl Ann Thompson, both of Davis, Calif.

[73] Assignee: Novo Nordisk Biotech, Inc., Davis, Calif.

[21] Appl. No.: 608,224

[22] Filed: Feb. 28, 1996

Related U.S. Application Data

[62] Division of Ser. No. 309,341, Sep. 20, 1994, Pat. No. 5,594,119.
[51] Int. Cl.$^6$ .............. C12N 15/00; C12N 1/14; C12N 1/16; C12N 1/18
[52] U.S. Cl. .............. 435/172.3; 435/254.11; 435/254.3
[58] Field of Search ............ 435/172.3, 254.11, 435/254.3

[56] References Cited

FOREIGN PATENT DOCUMENTS

WO 92/17595  10/1992  WIPO.

OTHER PUBLICATIONS

Sørensen et al., Carlsberg Res. Commun., vol. 54, pp. 193–202 (1989).
Jarai et al., Gene, vol. 145, pp. 171–178 (1994).
Frederick et al., Gene, vol. 125, pp. 57–64 (1993).
Svendsen et al., FEBS Letters, vol. 333, No. 1,2, pp. 39–43 (1993).
Woolford et al., Molecular & Cellular Biology, vol. 6, No. 7, pp. 2500–2510 (1986).
Mukhtar et al., Gene, vol. 121, pp. 173–177 (1992).
Ammerer et al., Molecular & Cellular Biology, vol. 6, No. 7, pp. 2490–2499 (1986).
Stevens et al., J. of Cell Biology, vol. 102, pp. 1551–1557 (1986).
Rodney Rothstein, Methods in Enzymology, vol. 194, pp. 281–301 (1991).
L. Valls et al., Cell, vol. 48, pp. 887–897 (1987).
Berka et al., Gene, vol. 86, No. 2, pp. 153–162 (1990).
Yaver et al., 34th Annual Meeting of ASCB, Molecular Biol. Cell, 5 (Suppl.) ISSN: 1059–1525 (1994).
Dal Degan et al. (1992) Appl. and Environ. Microbiol. 58(7): 2144–2152.
de Ruiter–Jacobs et al. (1989) Curr. Genetics 16: 159–163.
Krishnan et al. (1986) J. Chromatog. 370: 315–326.

*Primary Examiner*—Robert A. Wax
*Assistant Examiner*—Lisa J. Hobbs
*Attorney, Agent, or Firm*—Steve T. Zelson, Esq.; Elias J. Lambiris, Esq.

[57] ABSTRACT

The present invention relates to a gene encoding an ascomycete or deuteromycete carboxypeptidase Y gene, and host cells modified so as to produce reduced amounts of carboxypeptidase.

9 Claims, 13 Drawing Sheets

FIG. 1A

```
         10         20         30         40         50         60
TCCTCTGCCT ACTCATCCCA TCACCATCTC AATTCATACC GCCCCCGTGG GGTTTCAGCA CCA 69         78         87         96        105        114
    ATG AGA GTC CTT CCA GCT GCT ATG CTG GTT GGA GCG GCC ACG GCG GCC GTT CCT
    MET Arg Val Leu Pro Ala Ala MET Leu Val Gly Ala Ala Thr Ala Ala Val Pro 123        132        141        150        159        168
    CCC TTC CAG CAG GTC CTT GGA GGT AAC GGT GCC AAG CAC GGT GCC GAC CAT GCG
    Pro Phe Gln Gln Val Leu Gly Gly Asn Gly Ala Lys His Gly Ala Asp His Ala 177        186        195        204        213        222
    GCC GAG GTC CCT GCG GAT CAC AGT GCC GAC TCT GAC GGG TTC TCC AAG CCG CTG CAC GCA
    Ala Glu Val Pro Ala Asp His Ser Ala Asp Ser Asp Gly Phe Ser Lys Pro Leu His Ala 231        240        249        258        267        276
    TTC CAG GAG GAG CTG AAG TCT CTC TCT GAC TCT GAC GAG GCT CGT AAG CTT TGG GAT GAG
    Phe Gln Glu Glu Leu Lys Ser Leu Ser Asp Ser Asp Glu Ala Arg Lys Leu Trp Asp Glu 285        294        303        312        321        330
    GCC AGC TTC TTT CCG GAG AGC ATG GAT CAG AAC CCT CTC TTC TCC CTC CCC
    Val Ala Ser Phe Phe Pro Glu Ser MET Asp Gln Asn Pro Leu Phe Ser Leu Pro
```

FIG. 1B

```
     339         348         357         366         375         384
     |           |           |           |           |           |
AAG  AAC  CGC  CGT  CCC  GAC  TCG  CAC  GAC  CAC  ATC  GTC  CGC  GGC  TCC
Lys  Asn  Arg  Arg  Pro  Asp  Ser  His  Asp  His  Ile  Val  Arg  Gly  Ser 393         402         411         420         429         438
     |           |           |           |           |           |
GAC  GTT  CAG  AGC  GTC  TGG  GTC  ACT  GGT  GAG  AAC  GGT  GAG  AAG  GAG  CGC  GAG  GTC
Asp  Val  Gln  Ser  Val  Trp  Val  Thr  Gly  Glu  Asn  Gly  Glu  Lys  Glu  Arg  Glu  Val 447         456         465         474         483         492
     |           |           |           |           |           |
GAT  GGC  AAG  CTG  GAA  GCC  TAT  GAT  CTC  AGG  GTC  AAG  AAG  ACC  GAT  CCT  GGC  TCT
Asp  Gly  Lys  Leu  Glu  Ala  Tyr  Asp  Leu  Arg  Val  Lys  Lys  Thr  Asp  Pro  Gly  Ser 501         510         519         528         537         546
     |           |           |           |           |           |
CTT  GGC  ATC  GAC  CCC  GGC  GTG  AAG  CAG  TAC  ACC  GGT  TAT  CTC  GAT  GAC  AAC  GAG
Leu  Gly  Ile  Asp  Pro  Gly  Val  Lys  Gln  Tyr  Thr  Gly  Tyr  Leu  Asp  Asp  Asn  Glu 555         564
     |           |
AAT  GAT  AAG  CAT  TTG  TTC  TAC  T          GTAAGCACAC  CTTGGTTCAA  GATCACGCTT  TTTATATGCT
Asn  Asp  Lys  His  Leu  Phe  Tyr  Trp 621         631         641         650         659         668
     |           |           |           |           |           |
CTGGATATCT  AACGCAACTT  AG  GG  TTC  TTC  GAG  TCT  CGC  AAT  GAC  CCC  GAG  AAT  GAT
                            Phe  Phe  Glu  Ser  Arg  Asn  Asp  Pro  Glu  Asn  Asp
```

FIG. IC

```
677         686         695         704         713         722
 |           |           |           |           |           |
CCC GTT     CTG TGG     AAC GGT     CCT GGG     TGC TCT     TCC GGT     CTC ACC     GTT CTC
Pro Val     Leu Trp     Asn Gly     Gly Pro    Gly Cys     Ser Ser     Leu Thr     Gly Leu 731                     740                     749                     758                     767                     776
 |                       |                       |                       |                       |                       |
TTC ATG     GAG CTT     GGC CCT     AGC AGC     ATC AAC     AAG AAG     ATC CAG     CCG GTC     TAC AAT
Phe MET     Glu Leu     Gly Pro     Ser Ser     Ile Asn     Lys Lys     Ile Gln     Pro Val     Tyr Asn 785         794         803         812         821         830
 |           |           |           |           |           |
GAC TAC     GCT TGG     AAC TCC     AAC GCG     TCC GTG     ATC GTC     CAG CCT     GTC AAT
Asp Tyr     Ala Trp     Asn Ser     Asn Ala     Ser Val     Ile Phe     Gln Pro     Val Asn 839         848         857         866         875         884
 |           |           |           |           |           |
GTC GGT     TAC TCC     TAC AGT     AAC TCT     GCT GTC     TTT GAC     CTT GAC     AGC GTC     CCT GTC
Val Gly     Tyr Ser     Tyr Ser     Asn Ser     Ala Val     Ile Phe     Leu Asp     Thr Val     Ala Ala 893         902         911         920         929         938
 |           |           |           |           |           |
GTC GGT     TAC TCC     TAC TAC     AGT AAC     TCT GCT     GTC AGC     GAC ACG     GTC GCT     GCT GGC     AAG
Val Gly     Tyr Ser     Tyr Ser     Asn Ser     Ala Val     Ser Asp     Thr Val     Ala Ala     Gly Lys 947         956         965         974         983         992
 |           |           |           |           |           |
GAC GTC     TAT GCC     TTG CTT     ACC CTC     TTC TTC     AAA CAA     TTC CCC     GAG TAT     GCT AAG
Asp Val     Tyr Ala     Leu Leu     Thr Leu     Phe Phe     Lys Gln     Phe Pro     Glu Tyr     Ala Lys

CAG GAC     TTC CAC     ATT GCC     GGT GAA     TCT TAT     GCT GGT     CAC TAT     ATC CCC     GTC TTC
Gln Asp     Phe His     Ile Ala     Gly Glu     Ser Tyr     Ala Gly     His Tyr     Ile Pro     Val Phe
```

FIG. 1D

```
1001              1010            1019            1028            1037            1046
 |   GCT TCG GAG ATC CTG TCT CAC AAG AAG CGC AAC ATC AAC CTG CAG TCC GTT CTC
     Ala Ser Glu Ile Leu Ser His Lys Lys Arg Asn Ile Asn Leu Gln Ser Val Leu 1055              1064            1073            1082            1091            1100
 |   ATT GGC AAC GGT CTC GAC GGA TAC ACC CAG TAC GAG TAC TAC CGT CCC ATG
     Ile Gly Asn Gly Leu Thr Asp Gly Tyr Thr Gln Tyr Glu Tyr Tyr Arg Pro MET 1109              1118            1127            1136            1145            1154
 |   GCC TGC GGT GAC GGC GGT TAC CCA GCT GTC TTG GAC GAG AGC TCC TGC CAG TCC
     Ala Cys Gly Asp Gly Gly Tyr Pro Ala Val Leu Asp Glu Ser Ser Cys Gln Ser 1163              1172            1181            1190            1199            1208
 |   ATG GAC AAC GCT CTT CCT CGC TGC CAG TCT ATG ATT GAG TCT TGC TAC AGT TCC
     MET Asp Asn Ala Leu Pro Arg Cys Gln Ser MET Ile Glu Ser Cys Tyr Ser Ser 1217              1226            1235            1244            1253            1262
 |   GAG AGC GCT TGG GTT TGT GTC CCG GCC TCC ATC TAC TGT AAC AAC GCC CTC CTT
     Glu Ser Ala Trp Val Cys Val Pro Ala Ser Ile Tyr Cys Asn Asn Ala Leu Leu 1271              1280            1289            1298            1307            1316
 |   GCC CCT TAC CAG CGC ACT GGG CAG AAC GTC TAT GAT GTC CGT GGT AAG TGC GAG
     Ala Pro Tyr Gln Arg Thr Gly Gln Asn Val Tyr Asp Val Arg Gly Lys Cys Glu
```

FIG. 1E

```
      1325            1334            1343            1352            1361            1370
GAT AGC AAC CTT TGC TAC TCG GCT ATG GGC TAC GTC AGC GAC TAC CTG AAC
Asp Ser Asn Leu Cys Tyr Ser Ala MET Gly Tyr Val Ser Asp Tyr Leu Asn 1379            1388            1397            1406            1415            1424
AAG CCC GAA GTC ATC GAG GCT GTT GGC GCT GAG GTC AAC GGC TAC GAC TGC
Lys Pro Glu Val Ile Glu Ala Val Gly Ala Glu Val Asn Gly Tyr Asp Ser Cys 1433            1442            1451            1460            1469            1478
AAC TTT GAC ATC AAC CGC AAC TTC CTC TTC CAC GGT GAC TGG ATG AAG CCC TAC
Asn Phe Asp Ile Asn Arg Asn Phe Leu Phe His Gly Asp Trp MET Lys Pro Tyr 1487            1496            1505            1514            1523            1532
CAC CGC CTC GTT CCG GGA CTC CTG GAG CAG ATC CCT GTC TTG ATC TAT GCC GGT
His Arg Leu Val Pro Gly Leu Leu Glu Gln Ile Pro Val Leu Ile Tyr Ala Gly 1541            1550            1559            1568            1577            1586
GAT GCT GAT TTC ATT TGC AAC TGG CTG GGC AAC AAG GCC TGG ACT GAA GCC CTG
Asp Ala Asp Phe Ile Cys Asn Trp Leu Gly Asn Lys Ala Trp Thr Glu Ala Leu 1595            1604            1613            1622            1631            1640
GAG TGG CCC GGA CAG GCT GAA TAT GCC TCC GCT GAG CTG GAG GAT CTG GTC ATT
Glu Trp Pro Gly Gln Ala Glu Tyr Ala Ser Ala Glu Leu Glu Asp Leu Val Ile
```

FIG. 1F

```
      1649        1658        1667        1676        1685        1694
GTC GAC AAT GAG CAC ACG AAG AAG ATT GGC CAG GTT AAG TCC CAT GGC AAC
Val Asp Asn Glu His Thr Lys Lys Ile Gly Gln Val Lys Ser His Gly Asn 1703        1712        1721        1730        1739        1748
TTC ACC TTC ATG CGT CTC TAT GGT GGT GGC CAC ATG GTC CCG ATG GAC CAG CCC
Phe Thr Phe MET Arg Leu Tyr Gly Gly Gly His MET Val Pro MET Asp Gln Pro 1757        1766        1775        1784        1793              1809
GAG TCG AGT CTC GAG TTC TTC AAC CGC TGG TTG GGA GGT GAA TGG TTC TAA AGACGTGCTA
Glu Ser Ser Leu Glu Phe Phe Asn Arg Trp Leu Gly Gly Glu Trp Phe 1819        1829        1839        1849        1859        1869        1879
CCACCGCATA TAGACTTTCT GGTCATTTCG GTGACACTGC AGATATGTTT CTTAACGATA GTTTGAGCAT 1889        1899        1909        1919        1929        1939        1949
GCTTGTCAAT GCCCACTAGT CCCGATCCTT ATATGTTGCA TGTATCTAT GAGTTTGTC ACTATAGTGC 1959        1969        1979        1989        1999        2009        2019
ATTATACATG TGTACTTCGT ATGAGAATGA ATCGATCGCA TTTACACGCA TATAAATAGT ACCCACCTCC 2029        2039        2049        2059        2068
GCCTGGACAT GAATTAGGCC CGGCCAGTCG TTTACATACA GTGCTAGAA
```

FIG. 2A

```
          10         20         30         40         50         60         70
GCGGCCGCTG CTACTTGCTT TTTCTAATTT GATACTTTG TGTCCGTACC GTACCTTCCA GACCGCAAGG
          80         90        100        110        120        130    139
TACCCATCCT CTACCACTC ATCCCATCAT CATCTCGATT TCATACCAAC CCCGTTGGGT TTCAACACA
``` start of propeptide
                                                         1     193
                                                         ↓     ↓

| 148 | 157 | 166 | 175 | | | | | 238 | 247 |
|---|---|---|---|---|---|---|---|---|---|
| ATG | AGA GTT CTT CCA GCT ATG CTG GTT GCG GGC ACT GCG GCC GTC CCT |
| MET | Arg Val Leu Pro Ala MET Leu Val Gly Thr Ala Ala Val Pro |

| | | | | | | | | | 301 |
| CCC TTC CAG CAG GTC CTT GGA GGT AAC GGT CAC GGT GCC GAC CAT GCG |
| Pro Phe Gln Gln Val Leu Gly Gly Asn Gly His Gly Ala Asp His Ala |

| 256 | 265 | 274 | 283 | | | | | | 355 |
| GCC GAG GTC CCT GCG GAT CAC AGT GCC GAC GGG TTC TCC AAG CCG CTG CAC GCA |
| Ala Glu Val Pro Ala Asp His Ser Ala Asp Gly Phe Ser Lys Pro Leu His Ala |

| 310 | 319 | 328 | 337 | | | | | | |
| TTC CAG GAG CTG AAG TCT CTC GAT GAG GCT CGT AAG CTC TGG GAT GAG |
| Phe Gln Glu Leu Lys Ser Leu Asp Glu Ala Arg Lys Leu Trp Asp Glu |

FIG. 2B

```
    364                  373         382         391         400            409
    | GTT | GCT AGC | TTC CCG | GAG AGC | ATG GAT | CAG AAC | CCT CTC | TTC TCC | CTC CCC |
      Val   Ala Ser   Phe Pro   Glu Ser   MET Asp   Gln Asn   Pro Leu   Phe Ser   Leu Pro 418                  427         436         445         454            463
    | AAG | AAC AAC | CGC CGC | CCC GAC | CAC CAC | TGG GAC | CAC ATC | GTC CGC | GGC TCC |
      Lys   Lys Asn   Arg Arg   Pro Asp   His His   Trp Asp   His Ile   Val Arg   Gly Ser 472                  481         490         499         508            517
    | GAC | GTT ACT | AGC GTC | TGG GTT | CAG AGC | GAG AAC | GGT GAG | AAG GAG | CGT GAG | GTC
      Asp   Val Thr   Ser Val   Trp Val   Gln Ser   Glu Asn   Gly Glu   Lys Glu   Arg Glu   Val
                                                                    predicted N-teminus of mature CPY
    526                  535         544         553 ↓       562            571
    | AAG | CTG GAA | GCC TAT | GAT CTC | AGG GTC | AAG GTC | AAG ACC | GAT CCT | AGC TCT |
      Lys   Leu Glu   Ala Tyr   Asp Leu   Arg Val   Lys Val   Lys Thr   Asp Pro   Ser Ser 580                  589         598         607         616            625
    | GAT | GGC CCT | GAA CTG | CTG AGG | GTC AAG | GTC ACC | AAG GTT | GAT CCT | AGC TCT |
      Asp   Gly Lys   Leu Glu   Leu Arg   Val Lys   Val Thr   Lys Val   Asp Pro   Ser Ser

| CTT | GGC ATC | GAC CCT | GGT GTA | AAG TAC | ACC TAT | CTC TAT | GAT GAC | AAC GAG |
      Leu   Gly Ile   Asp Pro   Gly Val   Lys Tyr   Thr Tyr   Leu Tyr   Asp Asp   Asn Glu
```

*(Table shows DNA codon sequence with corresponding amino acid translation; arrow at position 553 marks the predicted N-terminus of mature CPY.)*

FIG. 2C

| | 634 | | 643 | | 652 | | 661 | | 670 | | 679 |
|---|---|---|---|---|---|---|---|---|---|---|---|
| AAC | AAG | CAT | CTG | TTC | TAC | TGG | TCT | CGC | AAT | GAC | CCC | GAG | AAT |
| Asn | Lys | His | Leu | Phe | Tyr | Trp | Ser | Arg | Asn | Asp | Pro | Glu | Asn |
| | 688 | | 697 | | 706 | | 715 | | 724 | | 733 |
| GAC | CCT | GTT | GTT | CTG | TGG | CTG | GGA | TGC | TCC | TCC | CTC | ACC | GGT |
| Asp | Pro | Val | Val | Leu | Trp | Leu | Gly | Cys | Ser | Ser | Leu | Thr | Gly |
| | 742 | | 751 | | 760 | | 769 | | 778 | | 787 |
| CTT | TTC | GAG | CTC | GGC | CCT | AGC | ATC | AAC | AAG | ATC | CAG | CCG | GTC | TAC |
| Leu | Phe | MET | Glu | Leu | Gly | Pro | Ser | Ile | Asn | Lys | Ile | Gln | Pro | Val | Tyr |
| | 796 | | 805 | | 814 | | 823 | | 832 | | 841 |
| AAC | GAC | TAC | GCT | TGG | AAC | TCC | GTG | ATC | TTC | CTT | GAC | CAG | CCT | GTC |
| Asn | Asp | Tyr | Ala | Trp | Asn | Ser | Val | Ile | Phe | Leu | Asp | Gln | Pro | Val |
| | 850 | | 859 | | 868 | | 877 | | 886 | | 895 |
| AAC | GTC | TAC | TCT | AAC | TCT | GCT | GTC | AGC | GAC | ACC | GTT | GCT | GGC |
| Asn | Val | Tyr | Ser | Asn | Ser | Ala | Val | Ser | Asp | Thr | Val | Ala | Gly |
| | 904 | | 913 | | 922 | | 931 | | 940 | | 949 |
| AAG | GGT | TAC | TAC | TTG | CTT | ACC | TTC | TTC | AAA | CAA | TTC | CCC | GAG | TAT | GCC |
| Asn | Gly | Tyr | Tyr | Leu | Leu | Thr | Phe | Phe | Lys | Gln | Phe | Pro | Glu | Tyr | Ala |
| AAG | GAC | TAT | GCC | | | | | | | | | | | | |
| Lys | Asp | Val | Tyr | Ala | | | | | | | | | | | |

FIG. 2D

```
         958       967       976       985       994      1003
         |         |         |         |         |         |
    AAG CAG GAC TTC CAC ATT GCC GGT GAA TCC TAT GCT GGT CAC TAT ATC CCC GTC
    Lys Gln Asp Phe His Ile Ala Gly Glu Ser Tyr Ala Gly His Tyr Ile Pro Val 1012      1021      1030      1039      1048      1057
         |         |         |         |         |         |
    TTT GCT TCG GAG ATT TTG TCT CAC AAG AAG CGC AAC ATC AAC CTG CAG TCC GTT
    Phe Ala Ser Glu Ile Leu Ser His Lys Lys Arg Asn Ile Asn Leu Gln Ser Val 1066      1075      1084      1093      1102      1111
         |         |         |         |         |         |
    CTT ATT GGC AAC GGT CTC ACC GAC GGT CTC ACT CAG TAC GAG TAC TAC CGT CCC
    Leu Ile Gly Asn Gly Leu Thr Asp Gly Leu Thr Gln Tyr Glu Tyr Tyr Arg Pro 1120      1129      1138      1147      1156      1165
         |         |         |         |         |         |
    ATG GCC TGT GGT GAC GGT GGT TAC CCA GCT GTC TTG GAC GAG GGC TCC TGC CAG
    MET Ala Cys Gly Asp Gly Gly Tyr Pro Ala Val Leu Asp Glu Gly Ser Cys Gln 1174      1183      1192      1201      1210      1219
         |         |         |         |         |         |
    GCC ATG GAC AAC GCC CTT CCT CGC TGC CAG TCT ATG ATT GAG TCT TGC TAT AGT
    Ala MET Asp Asn Ala Leu Pro Arg Cys Gln Ser MET Ile Glu Ser Cys Tyr Ser 1228      1237      1246      1255      1264      1273
         |         |         |         |         |         |
    TCC GAG AGC GCT TGG GTT GTC CCG GCC TCC ATC TAC TGT AAC AAC GCC CTC
    Ser Glu Ser Ala Trp Val Cys Val Pro Ala Ser Ile Tyr Cys Asn Asn Ala Leu
```

FIG. 2E

| 1282 | 1291 | 1300 | 1309 | 1318 | 1327 |
|---|---|---|---|---|---|
| CTT | GCC | CCT | TAC | CAG | AAC | CGC | ACC | GGA | CAG | AAC | GTC | TAC | GAT | GTT | CGT | GGT | AAG | TGC |
| Leu | Ala | Pro | Tyr | Gln | Arg | Thr | Gly | Gln | Asn | Val | Tyr | Asp | Val | Arg | Gly | Lys | Cys |

1336                                    1345                                    1354                                    1363                                    1372                                    1381

GAG GAT AGC TCC AAC CTC TGC TAC TCG GCC ATG GGC TAC GTC AGC GAC TAC CTG
Glu Asp Ser Ser Asn Leu Cys Tyr Ser Ala MET Gly Tyr Val Ser Asp Tyr Leu 1390                                    1399                                    1408                                    1417                                    1426                                    1435

AAC ACC GAG ATT GAG GCT GTT GGC GAG GTC AAC GGC TAC GAC TCG
Asn Lys Thr Glu Val Ile Glu Ala Val Gly Ala Glu Val Asn Gly Tyr Asp Ser 1444                                    1453                                    1462                                    1471                                    1480                                    1489

TGC AAC TTT GAC ATC AAC CGC AAC TTC CTC TTC CAC GGT GAC TGG ATG AAG CCC
Cys Asn Phe Asp Ile Asn Arg Asn Phe Leu Phe His Gly Asp Trp MET Lys Pro 1498                                    1507                                    1516                                    1525                                    1534                                    1543

TAC CAC CGT CTC GTT CCG GGA CTC CTG GAG CAG ATC CCT GTC CTG ATC TAC GCT
Tyr His Arg Leu Val Pro Gly Leu Leu Glu Gln Ile Pro Val Leu Ile Tyr Ala 1552                                    1561                                    1570                                    1579                                    1588                                    1597

GGT GAC GCC GAT TTC ATC TGC AAC TGG CTG GGC AAC AAG GCC TGG ACT GAA GCC
Gly Asp Ala Asp Phe Ile Cys Asn Trp Leu Gly Asn Lys Ala Trp Thr Glu Ala

FIG. 2F

```
      1606         1615         1624         1633         1642         1651
CTT  GAG  TGG  CCC  GGA  CAG  GCT  GAA  TAT  GCC  TCC  GCT  AAG  CTG  GAG  GAC  CTG  GTC
Leu  Glu  Trp  Pro  Gly  Gln  Ala  Glu  Tyr  Ala  Ser  Ala  Lys  Leu  Glu  Asp  Leu  Val 1660         1669         1678         1687         1696         1705
GTG  GTC  GAG  AAT  GAG  CAC  AAG  AAG  AAG  ATC  GGC  CAG  GTC  AAG  TCC  CAT  GGC
Val  Val  Glu  Asn  Glu  His  Lys  Lys  Lys  Ile  Gly  Gln  Val  Lys  Ser  His  Gly 1714         1723         1732         1741         1750         1759
AAC  TTC  ACC  TTC  ATG  CGT  CTC  TAT  GGC  GGT  GGC  CAC  ATG  GTC  CCG  ATG  GAC  CAA
Asn  Phe  Thr  Phe  MET  Arg  Leu  Tyr  Gly  Gly  Gly  His  MET  Val  Pro  MET  Asp  Gln 1768         1777         1786         1795         1804         1813
CCC  GAG  TCG  AGT  CTT  GAA  TTC  TTC  AAC  CGC  TGG  TTG  GGA  GGT  GAA  TGG  TTT  TAA
Pro  Glu  Ser  Ser  Leu  Glu  Phe  Phe  Asn  Arg  Trp  Leu  Gly  Gly  Glu  Trp  Phe 1823         1833         1843         1853         1863         1873         1883
AGACGTGCTA  TCACCGCATA  TAGACTTTCC  GGTCATTTCG  GTGACACTGC  AGATATGTTT  CTTAACGATA 1893         1903         1911         1923         1933         1943         1953
GTTTGAGGAT  GCTTGTCAAT  GCCCACTAAT  CCCGAGCCTT  ATGTTACATG  GTATCTATGA  GTTTGTCATT 1963         1973         1983         1993         2002
ATAGTGCATT  ATGCATTTGT  ACTCCGTACG  AGAATGAATC  AGCGGCCGC
```

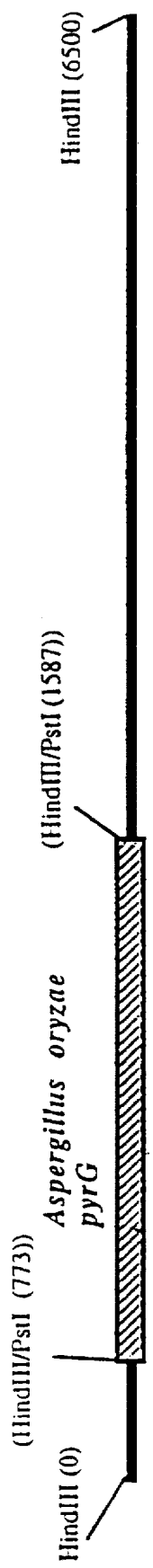
FIG.3 Construct for the disruption of CPY
= A. niger CPY gene
= A. oryzae pyrG
* # in parentheses correspond to base pairs in CPY fragment.

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 2068 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Aspergillus niger ( i x ) FEATURE:
    ( A ) NAME/KEY: intron
    ( B ) LOCATION: 572..632

( i x ) FEATURE:
    ( A ) NAME/KEY: CDS
    ( B ) LOCATION: join (571..633)

( x i ) SEQUENCE DESCRIPTION: SEQ ID NO: 1:

```
TCCTCTGCCT ACTCATCCCA TCACCATCTC AATTCATACC GCCCCCGTGG GGTTTCAGCA         60

CCA ATG AGA GTC CTT CCA GCT GCT ATG CTG GTT GGA GCG GCC ACG GCG         108
    Met Arg Val Leu Pro Ala Ala Met Leu Val Gly Ala Ala Thr Ala
    1           5                   10                  15

GCC GTT CCT CCC TTC CAG CAG GTC CTT GGA GGT AAC GGT GCC AAG CAC         156
Ala Val Pro Pro Phe Gln Gln Val Leu Gly Gly Asn Gly Ala Lys His
            20                  25                  30

GGT GCC GAC CAT GCG GCC GAG GTC CCT GCG GAT CAC AGT GCC GAC GGG         204
Gly Ala Asp His Ala Ala Glu Val Pro Ala Asp His Ser Ala Asp Gly
        35                  40                  45

TTC TCC AAG CCG CTG CAC GCA TTC CAG GAG GAG CTG AAG TCT CTC TCT         252
Phe Ser Lys Pro Leu His Ala Phe Gln Glu Glu Leu Lys Ser Leu Ser
    50                  55                  60

GAC GAG GCT CGT AAG CTT TGG GAT GAG GTG GCC AGC TTC TTC CCG GAG         300
Asp Glu Ala Arg Lys Leu Trp Asp Glu Val Ala Ser Phe Phe Pro Glu
65                  70                  75

AGC ATG GAT CAG AAC CCT CTC TTT TCC CTC CCC AAG AAG CAC AAC CGC         348
Ser Met Asp Gln Asn Pro Leu Phe Ser Leu Pro Lys Lys His Asn Arg
80                  85                  90                  95

CGT CCC GAC TCG CAC TGG GAC CAC ATC GTC CGC GGC TCC GAC GTT CAG         396
Arg Pro Asp Ser His Trp Asp His Ile Val Arg Gly Ser Asp Val Gln
            100                 105                 110

AGC GTC TGG GTC ACT GGT GAG AAC GGT GAG AAG GAG CGC GAG GTC GAT         444
Ser Val Trp Val Thr Gly Glu Asn Gly Glu Lys Glu Arg Glu Val Asp
        115                 120                 125

GGC AAG CTG GAA GCC TAT GAT CTC AGG GTC AAG AAG ACC GAT CCT GGC         492
Gly Lys Leu Glu Ala Tyr Asp Leu Arg Val Lys Lys Thr Asp Pro Gly
    130                 135                 140

TCT CTT GGC ATC GAC CCC GGC GTG AAG CAG TAC ACC GGT TAT CTC GAT         540
Ser Leu Gly Ile Asp Pro Gly Val Lys Gln Tyr Thr Gly Tyr Leu Asp
145                 150                 155

GAC AAC GAG AAT GAT AAG CAT TTG TTC TAC GTAAGCACAC CTTGGTTCAA           590
Asp Asn Glu Asn Asp Lys His Leu Phe Tyr
160                 165

GATCACGCTT TTTATATGCT CTGGATATCT AACGCAACTT AG TGG TTC TTC GAG          644
                                              Trp Phe Phe Glu
                                                  170

TCT CGC AAT GAC CCC GAG AAT GAT CCC GTT GTT CTG TGG CTG AAC GGT         692
Ser Arg Asn Asp Pro Glu Asn Asp Pro Val Val Leu Trp Leu Asn Gly
    175                 180                 185

GGC CCT GGG TGC TCT TCC CTC ACC GGT CTC TTC ATG GAG CTT GGC CCT         740
Gly Pro Gly Cys Ser Ser Leu Thr Gly Leu Phe Met Glu Leu Gly Pro
190                 195                 200                 205

AGC AGC ATC AAC AAG AAG ATC CAG CCG GTC TAC AAT GAC TAC GCT TGG         788
Ser Ser Ile Asn Lys Lys Ile Gln Pro Val Tyr Asn Asp Tyr Ala Trp
            210                 215                 220

AAC TCC AAC GCG TCC GTG ATC TTC CTT GAC CAG CCT GTC AAT GTC GGT         836
Asn Ser Asn Ala Ser Val Ile Phe Leu Asp Gln Pro Val Asn Val Gly
        225                 230                 235

TAC TCC TAC AGT AAC TCT GCT GTC AGC GAC ACG GTC GCT GCT GGC AAG         884
Tyr Ser Tyr Ser Asn Ser Ala Val Ser Asp Thr Val Ala Ala Gly Lys
    240                 245                 250
```

| | | | | | | | | | | | | | | | | |
|---|---|---|---|---|---|---|---|---|---|---|---|---|---|---|---|---|
|GAC|GTC|TAT|GCC|TTG|CTT|ACC|CTC|TTC|TTC|AAA|CAA|TTC|CCC|GAG|TAT|932|
|Asp|Val|Tyr|Ala|Leu|Leu|Thr|Leu|Phe|Phe|Lys|Gln|Phe|Pro|Glu|Tyr||
| |255| | | |260| | | | |265| | | | |  | |
|GCT|AAG|CAG|GAC|TTC|CAC|ATT|GCC|GGT|GAA|TCT|TAT|GCT|GGT|CAC|TAT|980|
|Ala|Lys|Gln|Asp|Phe|His|Ile|Ala|Gly|Glu|Ser|Tyr|Ala|Gly|His|Tyr||
|270| | | | |275| | | | |280| | | | |285| |
|ATC|CCC|GTC|TTC|GCT|TCG|GAG|ATC|CTG|TCT|CAC|AAG|AAG|CGC|AAC|ATC|1028|
|Ile|Pro|Val|Phe|Ala|Ser|Glu|Ile|Leu|Ser|His|Lys|Lys|Arg|Asn|Ile||
| | | | |290| | | | |295| | | | |300| | |
|AAC|CTG|CAG|TCC|GTT|CTC|ATT|GGC|AAC|GGT|CTC|ACC|GAC|GGA|TAC|ACC|1076|
|Asn|Leu|Gln|Ser|Val|Leu|Ile|Gly|Asn|Gly|Leu|Thr|Asp|Gly|Tyr|Thr||
| | | |305| | | | |310| | | | |315| | | |
|CAG|TAC|GAG|TAC|TAC|CGT|CCC|ATG|GCC|TGC|GGT|GAC|GGC|GGT|TAC|CCA|1124|
|Gln|Tyr|Glu|Tyr|Tyr|Arg|Pro|Met|Ala|Cys|Gly|Asp|Gly|Gly|Tyr|Pro||
| |320| | | | |325| | | | |330| | | | | |
|GCT|GTC|TTG|GAC|GAG|AGC|TCC|TGC|CAG|TCC|ATG|GAC|AAC|GCT|CTT|CCT|1172|
|Ala|Val|Leu|Asp|Glu|Ser|Ser|Cys|Gln|Ser|Met|Asp|Asn|Ala|Leu|Pro||
| |335| | | | |340| | | | |345| | | | | |
|CGC|TGC|CAG|TCT|ATG|ATT|GAG|TCT|TGC|TAC|AGT|TCC|GAG|AGC|GCT|TGG|1220|
|Arg|Cys|Gln|Ser|Met|Ile|Glu|Ser|Cys|Tyr|Ser|Ser|Glu|Ser|Ala|Trp||
|350| | | | |355| | | | |360| | | | |365| |
|GTT|TGT|GTC|CCG|GCC|TCC|ATC|TAC|TGT|AAC|AAC|GCC|CTC|CTT|GCC|CCT|1268|
|Val|Cys|Val|Pro|Ala|Ser|Ile|Tyr|Cys|Asn|Asn|Ala|Leu|Leu|Ala|Pro||
| | | | |370| | | | |375| | | | |380| | |
|TAC|CAG|CGC|ACT|GGG|CAG|AAC|GTC|TAT|GAT|GTC|CGT|GGT|AAG|TGC|GAG|1316|
|Tyr|Gln|Arg|Thr|Gly|Gln|Asn|Val|Tyr|Asp|Val|Arg|Gly|Lys|Cys|Glu||
| | | |385| | | | |390| | | | |395| | | |
|GAT|AGC|TCT|AAC|CTT|TGC|TAC|TCG|GCT|ATG|GGC|TAC|GTC|AGC|GAC|TAC|1364|
|Asp|Ser|Ser|Asn|Leu|Cys|Tyr|Ser|Ala|Met|Gly|Tyr|Val|Ser|Asp|Tyr||
| | |400| | | | |405| | | | |410| | | | |
|CTG|AAC|AAG|CCC|GAA|GTC|ATC|GAG|GCT|GTT|GGC|GCT|GAG|GTC|AAC|GGC|1412|
|Leu|Asn|Lys|Pro|Glu|Val|Ile|Glu|Ala|Val|Gly|Ala|Glu|Val|Asn|Gly||
| | |415| | | | |420| | | | |425| | | | |
|TAC|GAC|TCG|TGC|AAC|TTT|GAC|ATC|AAC|CGC|AAC|TTC|CTC|TTC|CAC|GGT|1460|
|Tyr|Asp|Ser|Cys|Asn|Phe|Asp|Ile|Asn|Arg|Asn|Phe|Leu|Phe|His|Gly||
|430| | | | |435| | | | |440| | | | |445| |
|GAC|TGG|ATG|AAG|CCC|TAC|CAC|CGC|CTC|GTT|CCG|GGA|CTC|CTG|GAG|CAG|1508|
|Asp|Trp|Met|Lys|Pro|Tyr|His|Arg|Leu|Val|Pro|Gly|Leu|Leu|Glu|Gln||
| | | | |450| | | | |455| | | | |460| | |
|ATC|CCT|GTC|TTG|ATC|TAT|GCC|GGT|GAT|GCT|GAT|TTC|ATT|TGC|AAC|TGG|1556|
|Ile|Pro|Val|Leu|Ile|Tyr|Ala|Gly|Asp|Ala|Asp|Phe|Ile|Cys|Asn|Trp||
| | | |465| | | | |470| | | | |475| | | |
|CTG|GGC|AAC|AAG|GCC|TGG|ACT|GAA|GCC|CTG|GAG|TGG|CCC|GGA|CAG|GCT|1604|
|Leu|Gly|Asn|Lys|Ala|Trp|Thr|Glu|Ala|Leu|Glu|Trp|Pro|Gly|Gln|Ala||
| | |480| | | | |485| | | | |490| | | | |
|GAA|TAT|GCC|TCC|GCT|GAG|CTG|GAG|GAT|CTG|GTC|ATT|GTC|GAC|AAT|GAG|1652|
|Glu|Tyr|Ala|Ser|Ala|Glu|Leu|Glu|Asp|Leu|Val|Ile|Val|Asp|Asn|Glu||
| |495| | | | |500| | | | |505| | | | | |
|CAC|ACG|GGC|AAG|AAG|ATT|GGC|CAG|GTT|AAG|TCC|CAT|GGC|AAC|TTC|ACC|1700|
|His|Thr|Gly|Lys|Lys|Ile|Gly|Gln|Val|Lys|Ser|His|Gly|Asn|Phe|Thr||
|510| | | | |515| | | | |520| | | | |525| |
|TTC|ATG|CGT|CTC|TAT|GGT|GGT|GGC|CAC|ATG|GTC|CCG|ATG|GAC|CAG|CCC|1748|
|Phe|Met|Arg|Leu|Tyr|Gly|Gly|Gly|His|Met|Val|Pro|Met|Asp|Gln|Pro||
| | | | |530| | | | |535| | | | |540| | |
|GAG|TCG|AGT|CTC|GAG|TTC|TTC|AAC|CGC|TGG|TTG|GGA|GGT|GAA|TGG|TTC|1796|
|Glu|Ser|Ser|Leu|Glu|Phe|Phe|Asn|Arg|Trp|Leu|Gly|Gly|Glu|Trp|Phe||
| | |545| | | | |550| | | | |555| | | | |
|TAA|AGACGTGCTA|CCACCGCATA|TAGACTTTCT|GGTCATTTCG|GTGACACTGC| | | | | | | | | | |1849|
|AGATATGTTT|CTTAACGATA|GTTTGAGCAT|GCTTGTCAAT|GCCCACTAGT|CCCGATCCTT| | | | | | | | | | |1909|

-continued

```
ATATGTTGCA TGGTATCTAT GAGTTTTGTC ACTATAGTGC ATTATACATG TGTACTTCGT  1969

ATGAGAATGA ATCGATCGCA TTTACACGCA TATAAATAGT ACCCACCTCC GCCTGGACAT  2029

GAATTAGGCC CGGCCAGTCG TTTACATACA GTGCTAGAA                         2068
```

( 2 ) INFORMATION FOR SEQ ID NO: 2:

( i ) SEQUENCE CHARACTERISTICS:
        ( A ) LENGTH: 557 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Aspergillus Niger ( x i ) SEQUENCE DESCRIPTION: SEQ ID NO: 2:

```
Met Arg Val Leu Pro Ala Ala Met Leu Val Gly Ala Ala Thr Ala Ala
 1               5                  10                  15

Val Pro Pro Phe Gln Gln Val Leu Gly Gly Asn Gly Ala Lys His Gly
                20                  25                  30

Ala Asp His Ala Ala Glu Val Pro Ala Asp His Ser Ala Asp Gly Phe
            35                  40                  45

Ser Lys Pro Leu His Ala Phe Gln Glu Glu Leu Lys Ser Leu Ser Asp
 50                  55                  60

Glu Ala Arg Lys Leu Trp Asp Glu Val Ala Ser Phe Phe Pro Glu Ser
 65                  70                  75                  80

Met Asp Gln Asn Pro Leu Phe Ser Leu Pro Lys Lys His Asn Arg Arg
                85                  90                  95

Pro Asp Ser His Trp Asp His Ile Val Arg Gly Ser Asp Val Gln Ser
            100                 105                 110

Val Trp Val Thr Gly Glu Asn Gly Glu Lys Glu Arg Glu Val Asp Gly
            115                 120                 125

Lys Leu Glu Ala Tyr Asp Leu Arg Val Lys Lys Thr Asp Pro Gly Ser
130                 135                 140

Leu Gly Ile Asp Pro Gly Val Lys Gln Tyr Thr Gly Tyr Leu Asp Asp
145                 150                 155                 160

Asn Glu Asn Asp Lys His Leu Phe Tyr Trp Phe Phe Glu Ser Arg Asn
                165                 170                 175

Asp Pro Glu Asn Asp Pro Val Val Leu Trp Leu Asn Gly Gly Pro Gly
            180                 185                 190

Cys Ser Ser Leu Thr Gly Leu Phe Met Glu Leu Gly Pro Ser Ser Ile
            195                 200                 205

Asn Lys Lys Ile Gln Pro Val Tyr Asn Asp Tyr Ala Trp Asn Ser Asn
210                 215                 220

Ala Ser Val Ile Phe Leu Asp Gln Pro Val Asn Val Gly Tyr Ser Tyr
225                 230                 235                 240

Ser Asn Ser Ala Val Ser Asp Thr Val Ala Gly Lys Asp Val Tyr
                245                 250                 255

Ala Leu Leu Thr Leu Phe Phe Lys Gln Phe Pro Glu Tyr Ala Lys Gln
            260                 265                 270

Asp Phe His Ile Ala Gly Glu Ser Tyr Ala Gly His Tyr Ile Pro Val
            275                 280                 285

Phe Ala Ser Glu Ile Leu Ser His Lys Lys Arg Asn Ile Asn Leu Gln
290                 295                 300
```

| | | | | | | | | | | | | | | | |
|---|---|---|---|---|---|---|---|---|---|---|---|---|---|---|---|
| Ser | Val | Leu | Ile | Gly | Asn | Gly | Leu | Thr | Asp | Gly | Tyr | Thr | Gln | Tyr | Glu |
| 305 | | | | | 310 | | | | 315 | | | | | | 320 |
| Tyr | Tyr | Arg | Pro | Met | Ala | Cys | Gly | Asp | Gly | Gly | Tyr | Pro | Ala | Val | Leu |
| | | | | 325 | | | | | 330 | | | | | 335 | |
| Asp | Glu | Ser | Ser | Cys | Gln | Ser | Met | Asp | Asn | Ala | Leu | Pro | Arg | Cys | Gln |
| | | | 340 | | | | | 345 | | | | | 350 | | |
| Ser | Met | Ile | Glu | Ser | Cys | Tyr | Ser | Ser | Glu | Ser | Ala | Trp | Val | Cys | Val |
| | | 355 | | | | | 360 | | | | | 365 | | | |
| Pro | Ala | Ser | Ile | Tyr | Cys | Asn | Asn | Ala | Leu | Leu | Ala | Pro | Tyr | Gln | Arg |
| | 370 | | | | | 375 | | | | | 380 | | | | |
| Thr | Gly | Gln | Asn | Val | Tyr | Asp | Val | Arg | Gly | Lys | Cys | Glu | Asp | Ser | Ser |
| 385 | | | | | 390 | | | | 395 | | | | | | 400 |
| Asn | Leu | Cys | Tyr | Ser | Ala | Met | Gly | Tyr | Val | Ser | Asp | Tyr | Leu | Asn | Lys |
| | | | | 405 | | | | | 410 | | | | | 415 | |
| Pro | Glu | Val | Ile | Glu | Ala | Val | Gly | Ala | Glu | Val | Asn | Gly | Tyr | Asp | Ser |
| | | | 420 | | | | | 425 | | | | | 430 | | |
| Cys | Asn | Phe | Asp | Ile | Asn | Arg | Asn | Phe | Leu | Phe | His | Gly | Asp | Trp | Met |
| | | 435 | | | | | 440 | | | | | 445 | | | |
| Lys | Pro | Tyr | His | Arg | Leu | Val | Pro | Gly | Leu | Leu | Glu | Gln | Ile | Pro | Val |
| | 450 | | | | | 455 | | | | | 460 | | | | |
| Leu | Ile | Tyr | Ala | Gly | Asp | Ala | Asp | Phe | Ile | Cys | Asn | Trp | Leu | Gly | Asn |
| 465 | | | | | 470 | | | | 475 | | | | | | 480 |
| Lys | Ala | Trp | Thr | Glu | Ala | Leu | Glu | Trp | Pro | Gly | Gln | Ala | Glu | Tyr | Ala |
| | | | | 485 | | | | | 490 | | | | | 495 | |
| Ser | Ala | Glu | Leu | Glu | Asp | Leu | Val | Ile | Val | Asp | Asn | Glu | His | Thr | Gly |
| | | | 500 | | | | | 505 | | | | | 510 | | |
| Lys | Lys | Ile | Gly | Gln | Val | Lys | Ser | His | Gly | Asn | Phe | Thr | Phe | Met | Arg |
| | | 515 | | | | | 520 | | | | | 525 | | | |
| Leu | Tyr | Gly | Gly | Gly | His | Met | Val | Pro | Met | Asp | Gln | Pro | Glu | Ser | Ser |
| | 530 | | | | | 535 | | | | | 540 | | | | |
| Leu | Glu | Phe | Phe | Asn | Arg | Trp | Leu | Gly | Gly | Glu | Trp | Phe | | | |
| 545 | | | | | 550 | | | | 555 | | | | | | |

( 2 ) INFORMATION FOR SEQ ID NO: 3:

( i ) SEQUENCE CHARACTERISTICS:
       ( A ) LENGTH: 2002 base pairs
       ( B ) TYPE: nucleic acid
       ( C ) STRANDEDNESS: double
       ( D ) TOPOLOGY: linear ( i i ) MOLECULE TYPE: cDNA ( v i ) ORIGINAL SOURCE:
       ( A ) ORGANISM: Aspergillus niger ( i x ) FEATURE:
       ( A ) NAME/KEY: intron
       ( B ) LOCATION: 349..411

( i x ) FEATURE:
       ( A ) NAME/KEY: CDS
       ( B ) LOCATION: join (348..412)

( x i ) SEQUENCE DESCRIPTION: SEQ ID NO: 3:

```
GCGGCCGCTG CTACTTGCTT TTTCTAATTT GATACTTTTG TGTCCGTACC GTACCTTCCA      60

GACCGCAAGG TACCCATCCT CTACCTACTC ATCCCATCAT CATCTCGATT TCATACCAAC     120

CCCGTTGGGT TTCAACACA ATG AGA GTT CTT CCA GCT GCT ATG CTG GTT GGA     172
                        Met Arg Val Leu Pro Ala Ala Met Leu Val Gly
                          1               5                      10
```

-continued

| | | | | | | | | | | | | | | | | |
|---|---|---|---|---|---|---|---|---|---|---|---|---|---|---|---|---|
| GCG | GGC | ACT | GCG | GCC | GTC | CCT | CCC | TTC | CAG | CAG | GTC | CTT | GGA | GGT | AAC | 220 |
| Ala | Gly | Thr | Ala 15 | Ala | Val | Pro | Pro 20 | Phe | Gln | Gln | Val | Leu | Gly 25 | Gly | Asn | |
| GGT | GCC | AAG | CAC | GGT | GCC | GAC | CAT | GCG | GCC | GAG | GTC | CCT | GCG | GAT | CAC | 268 |
| Gly | Ala | Lys 30 | His | Gly | Ala | Asp | His 35 | Ala | Ala | Glu | Val | Pro 40 | Ala | Asp | His | |
| AGT | GCC | GAC | GGG | TTC | TCC | AAG | CCG | CTG | CAC | GCA | TTC | CAG | GAG | GAG | CTG | 316 |
| Ser | Ala 45 | Asp | Gly | Phe | Ser | Lys 50 | Pro | Leu | His | Ala | Phe 55 | Gln | Glu | Glu | Leu | |
| AAG | TCT | CTC | TCT | GAT | GAG | GCT | CGT | AAG | CTC | TGG | GAT | GAG | GTT | GCT | AGC | 364 |
| Lys 60 | Ser | Leu | Ser | Asp | Glu 65 | Ala | Arg | Lys | Leu | Trp 70 | Asp | Glu | Val | Ala | Ser 75 | |
| TTC | TTC | CCG | GAG | AGC | ATG | GAT | CAG | AAC | CCT | CTC | TTC | TCC | CTC | CCC | AAG | 412 |
| Phe | Phe | Pro | Glu | Ser 80 | Met | Asp | Gln | Asn | Pro 85 | Leu | Phe | Ser | Leu | Pro 90 | Lys | |
| AAG | CAC | AAC | CGC | CGC | CCC | GAC | CAC | CAC | TGG | GAC | CAC | ATC | GTC | CGC | GGC | 460 |
| Lys | His | Asn | Arg 95 | Arg | Pro | Asp | His | His 100 | Trp | Asp | His | Ile | Val 105 | Arg | Gly | |
| TCC | GAC | GTT | CAG | AGC | GTC | TGG | GTT | ACT | GGT | GAG | AAC | GGT | GAG | AAG | GAG | 508 |
| Ser | Asp | Val 110 | Gln | Ser | Val | Trp | Val 115 | Thr | Gly | Glu | Asn | Gly 120 | Glu | Lys | Glu | |
| CGT | GAG | GTC | GAT | GGC | AAG | CTG | GAA | GCC | TAT | GAT | CTC | AGG | GTC | AAG | AAG | 556 |
| Arg | Glu 125 | Val | Asp | Gly | Lys | Leu 130 | Glu | Ala | Tyr | Asp | Leu 135 | Arg | Val | Lys | Lys | |
| ACC | GAT | CCT | AGC | TCT | CTT | GGC | ATC | GAC | CCT | GGC | GTA | AAG | CAG | TAC | ACC | 604 |
| Thr 140 | Asp | Pro | Ser | Ser | Leu 145 | Gly | Ile | Asp | Pro | Gly 150 | Val | Lys | Gln | Tyr | Thr 155 | |
| GGT | TAT | CTC | GAT | GAC | AAC | GAG | AAC | GAC | AAG | CAT | CTG | TTC | TAC | TGG | TTC | 652 |
| Gly | Tyr | Leu | Asp | Asp 160 | Asn | Glu | Asn | Asp | Lys 165 | His | Leu | Phe | Tyr | Trp 170 | Phe | |
| TTC | GAG | TCT | CGC | AAT | GAC | CCC | GAG | AAT | GAC | CCT | GTT | GTT | CTG | TGG | CTG | 700 |
| Phe | Glu | Ser | Arg 175 | Asn | Asp | Pro | Glu | Asn 180 | Asp | Pro | Val | Val | Leu 185 | Trp | Leu | |
| AAC | GGT | GGC | CCT | GGA | TGC | TCT | TCC | CTC | ACC | GGT | CTT | TTC | ATG | GAG | CTC | 748 |
| Asn | Gly | Gly 190 | Pro | Gly | Cys | Ser | Ser 195 | Leu | Thr | Gly | Leu | Phe 200 | Met | Glu | Leu | |
| GGC | CCT | AGC | AGC | ATC | AAC | AAG | AAG | ATC | CAG | CCG | GTC | TAC | AAC | GAC | TAC | 796 |
| Gly | Pro 205 | Ser | Ser | Ile | Asn | Lys 210 | Lys | Ile | Gln | Pro | Val 215 | Tyr | Asn | Asp | Tyr | |
| GCT | TGG | AAC | TCC | AAC | GCG | TCC | GTG | ATC | TTC | CTT | GAC | CAG | CCT | GTC | AAC | 844 |
| Ala | Trp 220 | Asn | Ser | Asn | Ala 225 | Ser | Val | Ile | Phe | Leu 230 | Asp | Gln | Pro | Val | Asn 235 | |
| GTC | GGT | TAC | TCT | TAC | AGC | AAC | TCT | GCT | GTC | AGC | GAC | ACC | GTT | GCT | GCT | 892 |
| Val | Gly | Tyr | Ser | Tyr 240 | Ser | Asn | Ser | Ala | Val 245 | Ser | Asp | Thr | Val | Ala 250 | Ala | |
| GGC | AAG | GAC | GTC | TAT | GCC | TTG | CTT | ACC | CTC | TTC | TTC | AAA | CAA | TTC | CCC | 940 |
| Gly | Lys | Asp | Val 255 | Tyr | Ala | Leu | Leu | Thr 260 | Leu | Phe | Phe | Lys | Gln 265 | Phe | Pro | |
| GAG | TAT | GCC | AAG | CAG | GAC | TTC | CAC | ATT | GCC | GGT | GAA | TCC | TAT | GCT | GGT | 988 |
| Glu | Tyr | Ala | Lys 270 | Gln | Asp | Phe | His 275 | Ile | Ala | Gly | Glu | Ser 280 | Tyr | Ala | Gly | |
| CAC | TAT | ATC | CCC | GTC | TTT | GCT | TCG | GAG | ATT | TTG | TCT | CAC | AAG | AAG | CGC | 1036 |
| His | Tyr | Ile | Pro 285 | Val | Phe | Ala | Ser | Glu 290 | Ile | Leu | Ser | His | Lys 295 | Lys | Arg | |
| AAC | ATC | AAC | CTG | CAG | TCC | GTT | CTT | ATT | GGC | AAC | GGT | CTC | ACC | GAC | GGT | 1084 |
| Asn | Ile | Asn | Leu 300 | Gln | Ser | Val | Leu | Ile 305 | Gly | Asn | Gly | Leu | Thr 310 | Asp | Gly 315 | |
| CTC | ACT | CAG | TAC | GAG | TAC | TAC | CGT | CCC | ATG | GCC | TGT | GGT | GAC | GGT | GGT | 1132 |
| Leu | Thr | Gln | Tyr | Glu 320 | Tyr | Tyr | Arg | Pro | Met 325 | Ala | Cys | Gly | Asp | Gly 330 | Gly | |

| | | | | | | | | | | | | | | | | |
|---|---|---|---|---|---|---|---|---|---|---|---|---|---|---|---|---|
| TAC | CCA | GCT | GTC | TTG | GAC | GAG | GGC | TCC | TGC | CAG | GCC | ATG | GAC | AAC | GCC | 1180 |
| Tyr | Pro | Ala | Val | Leu | Asp | Glu | Gly | Ser | Cys | Gln | Ala | Met | Asp | Asn | Ala | |
| | | | 335 | | | | 340 | | | | | 345 | | | | |
| CTT | CCT | CGC | TGC | CAG | TCT | ATG | ATT | GAG | TCT | TGC | TAT | AGT | TCC | GAG | AGC | 1228 |
| Leu | Pro | Arg | Cys | Gln | Ser | Met | Ile | Glu | Ser | Cys | Tyr | Ser | Ser | Glu | Ser | |
| | | 350 | | | | | 355 | | | | | 360 | | | | |
| GCT | TGG | GTT | TGT | GTC | CCG | GCC | TCC | ATC | TAC | TGT | AAC | AAC | GCC | CTC | CTT | 1276 |
| Ala | Trp | Val | Cys | Val | Pro | Ala | Ser | Ile | Tyr | Cys | Asn | Asn | Ala | Leu | Leu | |
| | 365 | | | | | 370 | | | | | 375 | | | | | |
| GCC | CCT | TAC | CAG | CGC | ACC | GGA | CAG | AAC | GTC | TAC | GAT | GTT | CGT | GGT | AAG | 1324 |
| Ala | Pro | Tyr | Gln | Arg | Thr | Gly | Gln | Asn | Val | Tyr | Asp | Val | Arg | Gly | Lys | |
| 380 | | | | | 385 | | | | | 390 | | | | | 395 | |
| TGC | GAG | GAT | AGC | TCC | AAC | CTC | TGC | TAC | TCG | GCC | ATG | GGC | TAC | GTC | AGC | 1372 |
| Cys | Glu | Asp | Ser | Ser | Asn | Leu | Cys | Tyr | Ser | Ala | Met | Gly | Tyr | Val | Ser | |
| | | | | 400 | | | | 405 | | | | | 410 | | | |
| GAC | TAC | CTG | AAC | AAG | ACC | GAG | GTC | ATT | GAG | GCT | GTT | GGC | GCT | GAG | GTC | 1420 |
| Asp | Tyr | Leu | Asn | Lys | Thr | Glu | Val | Ile | Glu | Ala | Val | Gly | Ala | Glu | Val | |
| | | | 415 | | | | 420 | | | | | 425 | | | | |
| AAC | GGC | TAC | GAC | TCG | TGC | AAC | TTT | GAC | ATC | AAC | CGC | AAC | TTC | CTC | TTC | 1468 |
| Asn | Gly | Tyr | Asp | Ser | Cys | Asn | Phe | Asp | Ile | Asn | Arg | Asn | Phe | Leu | Phe | |
| | | 430 | | | | | 435 | | | | | 440 | | | | |
| CAC | GGT | GAC | TGG | ATG | AAG | CCC | TAC | CAC | CGT | CTC | GTT | CCG | GGA | CTC | CTG | 1516 |
| His | Gly | Asp | Trp | Met | Lys | Pro | Tyr | His | Arg | Leu | Val | Pro | Gly | Leu | Leu | |
| | 445 | | | | | 450 | | | | | 455 | | | | | |
| GAG | CAG | ATC | CCT | GTC | CTG | ATC | TAC | GCT | GGT | GAC | GCC | GAT | TTC | ATC | TGC | 1564 |
| Glu | Gln | Ile | Pro | Val | Leu | Ile | Tyr | Ala | Gly | Asp | Ala | Asp | Phe | Ile | Cys | |
| 460 | | | | | 465 | | | | | 470 | | | | | 475 | |
| AAC | TGG | CTG | GGC | AAC | AAG | GCC | TGG | ACT | GAA | GCC | CTT | GAG | TGG | CCC | GGA | 1612 |
| Asn | Trp | Leu | Gly | Asn | Lys | Ala | Trp | Thr | Glu | Ala | Leu | Glu | Trp | Pro | Gly | |
| | | | | 480 | | | | 485 | | | | | 490 | | | |
| CAG | GCT | GAA | TAT | GCC | TCC | GCT | AAG | CTG | GAG | GAC | CTG | GTC | GTG | GTC | GAG | 1660 |
| Gln | Ala | Glu | Tyr | Ala | Ser | Ala | Lys | Leu | Glu | Asp | Leu | Val | Val | Val | Glu | |
| | | | 495 | | | | 500 | | | | | 505 | | | | |
| AAT | GAG | CAC | AAG | GGC | AAG | AAG | ATC | GGC | CAG | GTC | AAG | TCC | CAT | GGC | AAC | 1708 |
| Asn | Glu | His | Lys | Gly | Lys | Lys | Ile | Gly | Gln | Val | Lys | Ser | His | Gly | Asn | |
| | | 510 | | | | | 515 | | | | | 520 | | | | |
| TTC | ACC | TTC | ATG | CGT | CTC | TAT | GGC | GGT | GGC | CAC | ATG | GTC | CCG | ATG | GAC | 1756 |
| Phe | Thr | Phe | Met | Arg | Leu | Tyr | Gly | Gly | Gly | His | Met | Val | Pro | Met | Asp | |
| | 525 | | | | | 530 | | | | | 535 | | | | | |
| CAA | CCC | GAG | TCG | AGT | CTT | GAA | TTC | TTC | AAC | CGC | TGG | TTG | GGA | GGT | GAA | 1804 |
| Gln | Pro | Glu | Ser | Ser | Leu | Glu | Phe | Phe | Asn | Arg | Trp | Leu | Gly | Gly | Glu | |
| 540 | | | | | 545 | | | | | 550 | | | | | 555 | |
| TGG | TTT | TAA | AGACGTGCTA | TCACCGCATA | TAGACTTTCC | GGTCATTTCG | GTGACACTGC | | | | | | | | | 1863 |
| Trp | Phe | | | | | | | | | | | | | | | |
| AGATATGTTT | CTTAACGATA | GTTGAGGAT | GCTTGTCAAT | GCCCACTAAT | CCCGAGCCTT | | | | | | | | | | | 1923 |
| ATGTTACATG | GTATCTATGA | GTTTGTCATT | ATAGTGCATT | ATGCATTTGT | ACTCCGTACG | | | | | | | | | | | 1983 |
| AGAATGAATC | AGCGGCCGC | | | | | | | | | | | | | | | 2002 |

( 2 ) INFORMATION FOR SEQ ID NO: 4:

( i ) SEQUENCE CHARACTERISTICS:
        ( A ) LENGTH: 557 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Aspergilhus Niger ( x i ) SEQUENCE DESCRIPTION: SEQ ID NO: 4:

```
Met Arg Val Leu Pro Ala Ala Met Leu Val Gly Ala Gly Thr Ala Ala
 1               5                   10                  15
Val Pro Pro Phe Gln Gln Val Leu Gly Gly Asn Gly Ala Lys His Gly
                 20                  25              30
Ala Asp His Ala Ala Glu Val Pro Ala Asp His Ser Ala Asp Gly Phe
         35                  40                  45
Ser Lys Pro Leu His Ala Phe Gln Glu Glu Leu Lys Ser Leu Ser Asp
     50                  55                  60
Glu Ala Arg Lys Leu Trp Asp Glu Val Ala Ser Phe Phe Pro Glu Ser
 65                  70                  75                  80
Met Asp Gln Asn Pro Leu Phe Ser Leu Pro Lys Lys His Asn Arg Arg
                 85                  90                  95
Pro Asp His His Trp Asp His Ile Val Arg Gly Ser Asp Val Gln Ser
             100                 105                 110
Val Trp Val Thr Gly Glu Asn Gly Glu Lys Glu Arg Glu Val Asp Gly
         115                 120                 125
Lys Leu Glu Ala Tyr Asp Leu Arg Val Lys Lys Thr Asp Pro Ser Ser
    130                 135                 140
Leu Gly Ile Asp Pro Gly Val Lys Gln Tyr Thr Gly Tyr Leu Asp Asp
145                 150                 155                 160
Asn Glu Asn Asp Lys His Leu Phe Tyr Trp Phe Phe Glu Ser Arg Asn
                165                 170                 175
Asp Pro Glu Asn Asp Pro Val Val Leu Trp Leu Asn Gly Gly Pro Gly
                180                 185                 190
Cys Ser Ser Leu Thr Gly Leu Phe Met Glu Leu Gly Pro Ser Ser Ile
            195                 200                 205
Asn Lys Lys Ile Gln Pro Val Tyr Asn Asp Tyr Ala Trp Asn Ser Asn
    210                 215                 220
Ala Ser Val Ile Phe Leu Asp Gln Pro Val Asn Val Gly Tyr Ser Tyr
225                 230                 235                 240
Ser Asn Ser Ala Val Ser Asp Thr Val Ala Ala Gly Lys Asp Val Tyr
                245                 250                 255
Ala Leu Leu Thr Leu Phe Phe Lys Gln Phe Pro Glu Tyr Ala Lys Gln
            260                 265                 270
Asp Phe His Ile Ala Gly Glu Ser Tyr Ala Gly His Tyr Ile Pro Val
    275                 280                 285
Phe Ala Ser Glu Ile Leu Ser His Lys Lys Arg Asn Ile Asn Leu Gln
290                 295                 300
Ser Val Leu Ile Gly Asn Gly Leu Thr Asp Gly Leu Thr Gln Tyr Glu
305                 310                 315                 320
Tyr Tyr Arg Pro Met Ala Cys Gly Asp Gly Gly Tyr Pro Ala Val Leu
                325                 330                 335
Asp Glu Gly Ser Cys Gln Ala Met Asp Asn Ala Leu Pro Arg Cys Gln
            340                 345                 350
Ser Met Ile Glu Ser Cys Tyr Ser Ser Glu Ser Ala Trp Val Cys Val
        355                 360                 365
Pro Ala Ser Ile Tyr Cys Asn Asn Ala Leu Leu Ala Pro Tyr Gln Arg
    370                 375                 380
Thr Gly Gln Asn Val Tyr Asp Val Arg Gly Lys Cys Glu Asp Ser Ser
385                 390                 395                 400
Asn Leu Cys Tyr Ser Ala Met Gly Tyr Val Ser Asp Tyr Leu Asn Lys
                405                 410                 415
Thr Glu Val Ile Glu Ala Val Gly Ala Glu Val Asn Gly Tyr Asp Ser
```

|   |   |   | 420 |   |   |   |   | 425 |   |   |   | 430 |   |   |   |
|---|---|---|---|---|---|---|---|---|---|---|---|---|---|---|---|
| Cys | Asn | Phe 435 | Asp | Ile | Asn | Arg | Asn 440 | Phe | Leu | Phe | His | Gly 445 | Asp | Trp | Met |
| Lys | Pro 450 | Tyr | His | Arg | Leu | Val 455 | Pro | Gly | Leu | Leu | Glu 460 | Gln | Ile | Pro | Val |
| Leu 465 | Ile | Tyr | Ala | Gly | Asp 470 | Ala | Asp | Phe | Ile | Cys 475 | Asn | Trp | Leu | Gly | Asn 480 |
| Lys | Ala | Trp | Thr | Glu 485 | Ala | Leu | Glu | Trp | Pro 490 | Gly | Gln | Ala | Glu | Tyr 495 | Ala |
| Ser | Ala | Lys | Leu 500 | Glu | Asp | Leu | Val | Val 505 | Val | Glu | Asn | Glu | His 510 | Lys | Gly |
| Lys | Lys | Ile 515 | Gly | Gln | Val | Lys | Ser 520 | His | Gly | Asn | Phe | Thr 525 | Phe | Met | Arg |
| Leu | Tyr 530 | Gly | Gly | Gly | His | Met 535 | Val | Pro | Met | Asp | Gln 540 | Pro | Glu | Ser | Ser |
| Leu 545 | Glu | Phe | Phe | Asn | Arg 550 | Trp | Leu | Gly | Gly | Glu 555 | Trp | Phe |   |   |   |

GENE ENCODING CARBOXYPEPTIDASE OF *ASPERGILLUS NIGER*

This is a divisional application of application Ser. No. 08/309,341, filed Sep. 20, 1994, now U.S. Pat. No. 5,594,119, the contents of which are incorporated herein by reference in their entirety.

FIELD OF THE INVENTION

The present invention relates to a gene encoding a fungal vacuolar protease. In particular, the invention relates to a carboxypeptidase gene of a filamentous ascomycete or deuteromycete fungus, such as those of the genus Aspergillus.

BACKGROUND OF THE INVENTION

The fungal vacuole is an acidic organelle that contains many hydrolases, including several proteases, and is essentially equivalent to the mammalian lysosome. Several of the hydrolases have been identified and characterized in one or more species of fungi, particularly in yeast; these include protease A(PEP4 or PrA), protease B(PrB), aminopeptidase (APE), dipeptidyl aminopeptidase B(DPAP B), carboxypeptidase Y(CPY), and carboxypeptidase S(CPS). Most of the vacuolar hydrolases are glycoproteins which are synthesized as inactive precursors. In fact, all the aforementioned proteases with the exception of APE have signal peptides that lead to transit through the secretory pathway. In the late golgi, vacuolar proteins are sorted from secretory proteins and eventually delivered to the vacuole. In addition to a signal peptide, most vacuolar proteins also have a propeptide which is cleaved upon delivery to the vacuole to generate the mature active enzyme. It has been demonstrated that the amino acid information in PrA and CPY required for vacuolar targeting is present within the propeptide (Johnson et al., Cell 48: 875–885, 1987; Rothman et al. PNAS USA 83: 3248–3252, 1989; Valls et al., Cell 48: 887–897, 1989; Valls et al. J. Cell Biol. 111: 361–368, 1987). For CPY a string of four amino acid residues (QRPL) has been shown to be required for localization to the vacuole (Valls et al., J. Cell Biol. 111: 361–368, 1990). Once delivered to the vacuole, proteinase A (pep4) cleaves the propeptide of CPY and PrB leading to the activation of the proteases (Ammerer et al., Mol. Cell. Biol. 6: 2490–2499, 1986; Woolford et al., Mol. Cell. Biol. 6: 2500–2510, 1986).

In *S. cerevisiae*, three classes of mutants which mislocalize or missort vacuolar proteins have been identified (Bankaitis et al., PNAS USA 83: 9075–9079, 1986; Robinson et al., Mol. Cell. Biol., 8: 4936–4948, 1988; Rothman et al., EMBO J. 8: 2057–2065, 1989; Rothman and Stevens, Cell 47: 1041–1051, 1986). These mutants are called vps or vacuolar protein sorting mutants. Several of these mutants are isolated using a selection based on the observation that overexpression of a vacuolar protease due to a high copy number on a plasmid leads to a secretion of vacuolar proteases. (Stevens et al., J. Cell Biol. 102: 1551–1557, 1986; Rothman et al. PNAS USA 83: 3248–3242, 1986). This suggests that it is possible to saturate the sorting machinery within the late golgi.

In *S. cerevisiae*, it has also been demonstrated that strains deleted for PEP4, CPY and PrB produce higher levels of heterologous proteins due to a decrease in proteolysis of the desired product. Therefore, the vacuolar proteases in question are important from a commercial point of view because many of the fungi which produce them are used for recombinant production of heterologous proteins. The presence of these proteases in fermentation is undesirable, in that they can degrade the protein of interest, thereby significantly reducing yield. Elimination of the function of any given protease is facilitated by the disruption or deletion of the gene encoding it; however, doing so first requires identification and isolation of the corresponding gene in the host species of interest. As noted above, a few such genes have been isolated from various yeast strains; however, the genes encoding vacuolar proteases in the filamentous ascomycetes or deuteromycetes are less well known. For example, PEPC (Frederick et al., Gene 125: 57–64, 1993) and PEPE (Jarai et al., Gene 145: 171–178, 1994) genes coding for two other vacuolar proteases from *Aspergilus niger* have been isolated. PEPC codes for a proteinase B(PrB) homologue, and PEPE codes for a proteinase A homologue. The gene PEP4 from *Neurospora crassa* coding for a PrA homologue has also been cloned (Bowman, 17th Fungal Genetics Conference, 1993). For the first time herein is described the gene encoding a vacuolar CPY from a filamentous ascomycete or deuteromycete.

SUMMARY OF THE INVENTION

The present invention relates to a nucleic acid construct comprising a sequence encoding a filamentous ascomycete or deuteromycete carboxypeptidase Y, as well as the recombinantly produced protein encoded thereby. As used herein, "nucleic acid construct" is intended to indicate any nucleic acid molecule of cDNA, genomic DNA, synthetic DNA or RNA origin. The term "construct" is intended to indicated a nucleic acid segment which may be single- or double-stranded, and which may be isolated in complete or partial form from a naturally occurring gene or which has been modified to contain segments of DNA which are combined and juxtaposed in a manner which would not otherwise exist in nature. The construct may optionally contain other nucleic acid segments. In a preferred embodiment, the sequence encodes a carboxypeptidase of the genus Aspergillus. The invention also provides a method for producing a non-carboxypeptidase-producing filamentous ascomycete or deuteromycete cell, which comprises disrupting or deleting the carboxypeptidase gene so as to prevent the expression of a functional enzyme, or treating the gene by classical mutagenesis using physical or chemical treatments to generate cells which are reduced or lacking in their ability to produce CPY. In addition, the invention also encompasses a filamentous ascomycete or deuteromycete which is unable to produce a functional carboxypeptidase enzyme, or which produces the carboxypeptidase in reduced amounts relative to the amount produced by the wild-type strain. Such organisms provide the basis for an improved method of recombinant protein production, wherein the carboxypeptidase-deficient microorganism is transformed with the nucleic acid construct encoding the protein of interest, and cultured under conditions conducive to the expression of the protein.

BRIEF DESCRIPTION OF THE FIGURES

FIG. 1 illustrates the DNA sequence and translation of the *A. niger* Bo-1 genomic CPY clone.

FIG. 2 illustrates the DNA sequence and translation of *A. niger* SFAG 2 CPY cDNA. The predicted site for signal peptidase cleavage and the N-terminus of mature CPY are indicated.

FIG. 3 illustrates the construct used in disruption CPY.

DETAILED DESCRIPTION OF THE INVENTION

Attempts to isolate an Aspergillus carboxypeptidase Y are initiated by designing a series of degenerate oligonucleotides, using the sequences of *S. cerevisiae* CPY, *Penicillium janthinellum* carboxypeptidase S1 (Svedsen et al., FEBS 333: 39–43, 1993, and malt carboxypeptidase-MIII (Sørensen et al., Carlsberg Res. Commun. 54: 193–202, 1993). The oligonucleotide sequences are provided the examples below. These sequences are used as primers in various combinations in a PCR reaction using *Aspergillus niger* strain Bo-1 genomic DNA as a template. Two of the reactions (with primers 1-1 and 2-1; and 1-2 and 2-2) yield an 1100 bp amplification product, which is subcloned and sequenced, but none of the subclones has significant homology to CPY to be identified as the gene of interest.

Further PCR reactions with primers 3-1, 3-2, 4-1, 4-2, 2-1 and 2-2 are then made. In two of the reactions (primers 4-1 and 2-1; and 4-2 and 2-1) a 600 bp amplification product is obtained. This product is subcloned and 11 of the subclones sequenced; nine of these subclones are identical, and have homology to carboxypeptidaseY genes from other sources. The insert from one of the subclones is used to probe *A. niger* genomic DNA; hybridization with single bands is observed with BamHI, HindIII, and SalI digests, suggesting that a single CPY gene exists in *A. niger*. Hybridizations are done at 65° C. in 1.5× SSPE, 1.0% SDS, 0.5% non-fat milk and 200 µg/ml salmon sperm DNA.

An *A. niger* genomic DNA bank in EMBL4 is prepared and probed with the PCR CPY-derived gene fragment ($^{32}$P-labeled), in order to isolate a full length gene. Out of approximately 28,000 plaques, 11 positives are picked; nine of these still hybridize with the probe after purification. A 5.5 HindIII fragment common to a majority of these clones is identified as the *A. niger* CPY gene. This fragment is subcloned and sequenced; the sequence of the fragment, including the CPY coding region and predicted amino acid sequence, is provided in FIG. 1.

Subsequently, a cDNA bank from a different *A. niger* strain is also screened. At least one full-length clone is identified from this library as well. This clone is sequenced and the sequence is depicted in FIG. 2. Both DNA sequences predict a CPY precursor of 557 amino acids in length. Based on a comparison with the homologous gene from *S. cerevisiae*, CPY from *A. niger* appears to have a prepropeptide of 137 or 138 amino acids. The gene contains one intron of 61 base pairs. A comparison of the two *A. niger* sequences will show some difference in amino acid sequence, which presumably reflects the different strains from which the genomic and cDNA clones are isolated. A comparison with the amino acid sequences of the corresponding CPY genes of *S. cerevisiae* and *C. albicans* shows a 65% and 66% identity, respectively.

The present invention is not limited to the use of the sequences disclosed in FIGS. 1 and 2. First, the invention also encompasses nucleotide sequences which produce the same amino acid sequence as depicted in FIGS. 1 or 2, but differ by virtue of the degeneracy of the genetic code. In addition, the difference in amino acid sequence shown for two strains of the same species shows that variation within the sequence of a single species is tolerated, and using the techniques described herein, such variants can readily be identified. Therefore, when "*A. niger*" is referred to in this context, it will be understood to encompass all such variations. In particular, the invention also encompasses any variant nucleotide sequence, and the protein encoded thereby, which protein retains at least about an 80%, preferably about 85%, and most preferably at least about 90–95% homology with the amino acid sequence depicted in FIGS. 1 or 2, and which qualitatively retains the activity of the sequence described herein. Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln.

In addition, the isolated gene provides a means for isolating homologous genes from other filamentous ascomycetes or deuteromycetes, such as other Aspergillus species, e.g., *A. oryzae*, *A. foetidus*, *A. japonicus*, *A. aculeatus*, or *A. nidulans*. Other non-Aspergillus filamentous ascomycete species include Fusarium species, such as *F. graminearum*, *F. oxysporum*, *F. solani*, *F. culmorum* (or corresponding teleomorphs) *Neurospora crassa*, *Trichoderma reesei*, *T. viridae*, *T. harzianum*, *T. longibranchiatum*, *Penicillium janthinellum*, *P. notatum*, *P. chrysogenum*, *P. camemberti*, *P. roqueforti*, *Humicola insolen*, *H. grisea var. thermoidea*, *H. lanuginosa*, *Scytalidium thermophilum*, *Myceliophthora thermophila*, and *Thielavia terrestris*. The gene, or an oligonucleotide based thereon, can be used as probes in southern hybridization to isolate homologous genes of these other species. In particular, such probes can be used under low to high stringency conditions (for example, prehybridization and hybridization at 42° C. in 5× SSPE, 0.3% SDS, 200 µg/ml sheared and denatured salmon sperm DNA, and either 50, 35 or 25% formamide for high, medium and low stringencies, respectively) for hybridization with the genomic or cDNA of the species of interest, following standard southern blotting procedures, in order to identify and isolate the corresponding CPY gene therein. A PCR reaction using the degenerate probes mentioned herein and genomic DNA or first-strand cDNA from a filamentous fungus may also yield a CPY-specific product which could then be used as a probe to clone the corresponding genomic or cDNA.

The present gene is particularly useful in the creation of carboxypeptidase-deficient mutants of filamentous ascomycetes such as Aspergillus. This can be achieved in a number of ways. In one method, as described in further detail below, a selectable marker is cloned into the middle of the CPY gene. The disrupted fragment is then released from the parental plasmid using restriction enzymes. The linearized DNA fragment is used to transform the chosen host cell. In the host cell, the homologous ends pair with the host cell chromosome, and the homologous recombination results in a chromosomal gene replacement. Useful selectable markers for use with fungal cell hosts include amdS, pyrG, argB, niaD, sC, and hygB. Alternately, a two-step process can be employed using a two-way selectable marker. In such a process, a plasmid containing a truncated CPY gene and the selectable marker gene is digested with a restriction enzyme which cuts once within the the CPY fragment in order to target integration to the CPY locus during transformation. The transformants are then grown on media which will select for the loss of the selectable marker gene, e.g., when the marker is pyrG, the medium may contain 5-fluorootic acid. The loss of the selectable gene usually occurs by a recombination between the wild type CPY and the introduced truncated CPY gene. Approximately 50% of the resulting strain should have only the truncated CPY gene while the other 50% will contain only the wild type gene. Such methods are described in Rothstein, Meth. Enzymol. 194, 281–301, 1991.

The CPY-deficient mutants so created are particularly useful in the expression of heterologous protein. By "heterologous protein" in the present context is meant a protein which is not native to the host cell, a native protein in which modifications have been made to alter the native sequence, or a native protein whose expression is quantitatively altered as a result of a manipulation of the host cell by recombinant DNA techniques. Also encompassed within this term are native proteins for which expression in the mutants involves the use of genetic elements not native to the host cell, or use of native elements which have been manipulated to function in a manner not normally seen in the host cell.

As already noted, the production of proteases by a chosen host cell can severely limit the yield of the desired protein by degrading the product before it can be recovered. The elimination or reduction in the amount of CPY produced by a host can therefore substantially increase the yield of any given protein, and can render an otherwise commercially unsuitable host cell commercially feasible for recombinant protein production. In a preferred embodiment, the CPY deficient cells produce at least 25% less, preferably at least 50% less, and most preferably at least 70% less CPY, up to total loss of CPY function, than the corresponding wild-type strain.

The mutant fungal cells of the present invention can be used in recombinant protein production in the same manner as the wild-type strains. Those skilled in the art will readily recognize routine variations from the specific embodiments described herein which are useful in adapting the methodology to the strains noted above. A gene of interest can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the expressed protein, nucleotides encoding a signal sequence may be inserted prior to the coding sequence of the gene. For expression under the direction of control sequences, a gene to be used according to the invention is operably linked to the control sequences in the proper reading frame.

The expression vector may be any vector which may conveniently be subjected to recombinant DNA procedures, and the choice of vector will typically depend on the host cell into which it is to be introduced. In a preferred embodiment of the present invention, the host cell is a strain of the genus Aspergillus. Thus, the vector may be an autonomously replicating vector, i.e. a vector which exists as an extrachromosomal entity, the replication of which is independent of chromosomal replication, e.g. a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the sequence of the gene of interest should be operably connected to a suitable promoter sequence. The promoter may be any DNA sequence which shows transcriptional activity in the host cell of choice and may be derived from genes encoding proteins either homologous or heterologous to the host cell. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (glaA), *Rhizomucor miehei* lipase, *A. oryzae* alkaline protease, *A. oryzae* triose phosphate isomerase or *A. nidulans* acetamidase. Preferred are the TAKA-amylase and glaA promoters.

The expression vector of the invention may also comprise a suitable transcription terminator and, in eukaryotes, polyadenylation sequences operably connected to the DNA sequence encoding the heterologous gene sequence. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, or one which confers antibiotic resistance such as ampicillin, kanamycin, chloramphenicol or tetracycline resistance. Examples of Aspergillus selection markers include amdS, pyrG, argB, niaD, sC, and hygB, a marker giving rise to hygromycin resistance. Preferred for use in an Aspergillus host cell are the amdS and pyrG markers of *A. nidulans* or *A. oryzae*. Furthermore, selection may be accomplished by co-transformation, e.g. as described in WO 91/17243.

It is generally preferred that the expression gives rise to a product which is extracellular. The protein of interest may thus comprise a preregion permitting secretion of the expressed protein into the culture medium. If desirable, this preregion may be native to the protein of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from *Rhizomucor miehei*, the gene for the α-factor from *Saccharomyces cerevisiae* or the calf preprochymosin gene. Particularly preferred, when the host is a fungal cell, is the preregion for *A. oryzae* TAKA amylase, *A. niger* neutral amylase, the maltogenic amylase form Bacillus NCIB 11837, *B. stearothermophilus* α-amylase, or *Bacillus licheniformis* subtilisin. An effective signal sequence is the *A. oryzae* TAKA amylase signal, the *Rhizomucor miehei* aspartic proteinase signal and the *Rhizomucor miehei* lipase signal.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. Molecular Cloning, 1989).

The CPY-deficient mutants can be used to express any prokaryotic or eukaryotic protein of interest, and are preferably used to express eukaryotic proteins. Of particular interest for these cells is their use in expression of fungal enzymes such as catalase, laccase, phenoloxidase, oxidase, oxidoreductases, cellulase, xylanase, peroxidase, lipase, hydrolase, esterase, cutinase, protease and other proteolytic enzymes, aminopeptidase, carboxypeptidase, phytase, lyase, pectinase and other pectinolytic enzymes, amylase, glucoamylase, α-galactosidase, β-galactosidase, α-glucosidase, β-glucosidase, mannosidase, isomerase, invertase, transferase, ribonuclease, chitinase, and deoxyribonuclease. It will be understood by those skilled in the art that the term "fungal enzymes" includes not only native fungal enzymes, but also those fungal enzymes which have been modified by amino acid substitutions, deletions, additions, or other modifications which may be made to enhance activity, thermostability, pH tolerance and the like. The mutants can also be used to express heterologous proteins of pharmaceutical interest such as hormones, growth factors, receptors, and the like.

The invention will be further illustrated by the following non-limiting examples.

EXAMPLES

I. ISOLATION OF THE ASPERGILLUS NIGER CPY GENE

A. MATERIALS AND METHODS i. Strains

The following biological materials are used in the procedures described below. *Escherichia coli* K802 (ek4-(nrca), mcrB, hsdR2, galK2, GalT22, supE44, metB1; *E. coli* SOLR(E14-(mcrA)Δ(mcrCB-hsdSMR-mr$^r$)171, sbcC, recB, recJ, uvrC, umuC::Tn5(kan$^r$), lac, gyrA96, relA1, thi-1, endA1, λ$^R$[F'proABlacIqZΔM15]Su$^-$, *E. coli* JM101supE, thi-1, Δ(lac-proAB), [F'traD36, proAB, lacIqZΔM15], *E. coli* XL-1 Blue recA1, endA1, gyrA96, thi-1, hsdR17, supE44, relA1, lac, [F'proAB, lacIqZΔM15, Tn10 (tet$^R$)], *Aspergillus niger* Bo-1, *A. niger* SFAG-2.

ii. PCR amplification

PCR reactions are run using standard protocols with annealing steps done at 45° C. *A. niger* Bo-1 genomic DNA is used as template and the following degenerate oligonucleotides are used.

Primer 1-1(94-282)-GGIGGICCIGGITGYTC
Primer 1-2(94-283)-GGIGGICCIGGITGYAG
Primer 2-1(94-284)-CCIAGCCARTTRCADAT
Primer 2-2(94-285)-CCYAACCARTTRCADAT
Primer 3-1(94-331)-GTIGGITTYTCITAYTCIGG
Primer 3-2(94-332)-GTIGGITTYAGYTAYAGYGG
Primer 4-1(94-329)-GARTCITAYGCIGGICAYTA
Primer 4-2(94-330)-GARAGYTAYGCIGGICAYTA In the above primers, I stands for inosine, Y for C or T, R for A or G, and D for A, G or T.

iii. Subcloning PCR products

PCR products are subcloned for sequencing using the TA Cloning Kit (Invitrogen) following the manufacturer's protocols.

iv. In vivo excision from Lambda Zap II

From the CPY cDNA Lambda Zap clones, a plasmid is rescued containing the cDNA inserts in a pBluescript SK-vector by passage through the *E. coli* strain SOLR following the protocols provided by Stratagene.

v. DNA sequencing

Nucleotide sequencing is determined using TAQ polymerase cycle-sequencing with fluorescent labeled nucleotides. The sequencing reactions are electrophoresed on an Applied Biosystems automatic DNA sequencer (Model 363A, version 1.2.0). The following CPY specific primers are used, in addition to the M13 reverse (-48) and M13 (-20) forward primers (Sanger et al., J. Mol. Biol. 143: 163–178):

94-376 TCGCTGCCAGTCTATGATTGA
94-377 ACATCAACCGCAACTTCCTCT
94-378 TTGCCAATGAGAACGGACTGC
94-379 CGCACTTACCACGGACATCAT
94-503 CAAGCATCCTCAAACTATCGT
94-504 GAGACGCATGAAGGTGAAGTT
94-505 GCCGTCCCTCCCTTCCAGCAG
94-506 GTGCCGACGGGTTCTCCAAGC
94-507 GCAGCGAGGAAGAGCGTTGTC
94-510 GGGTCATTCTCGGGGTCATTG
94-511 GACCCCGAGAATGACCCTGTT
94-512 GTAGGGCTTCATCCAGTCACC
94-513 TCTCACCGTTCTCACCAGTAA
94-514 TCCCTCCCCAAGAAGCACAAC
94-528 AGCGTCTGGGTTACTGGTGAG
94-529 AAGATCGGCCAGGTCAAGTCC
94-530 GAGACGGTGGTAGGGCTTCAT
94-531 AACGTCGGTTACTCTTACAGC
94-532 GTGGTCGGGGCGGCGGTTGTG
94-533 TGTTTGAAGAAGAGGGTAAGC
94-575 CGCTGCTACTTGATTTTTCTA
94-576 CTCAGCGCCAACAGCCTCAAT
94-577 ACCTGCAGTCCGTTCTTATTG
94-634 TGCGATCGATTCATTCTCATC
94-635 GGAGTAACCGACATTGACAGG
94-636 CCTGTCAATGTCGGTTACTCC
94-637 GTCCCATGGCAACTTCACCTT
94-646 CTTCTCACCGTTCTCACCAGT
94-647 CGAGACTCGAAGAACCCTAAG

B. RESULTS

Using *A. niger* Bo-1 genomic DNA as template PCR reactions are done using various combinations of the CPY specific degenerate oligonucleotides, primers 1-1, 1-2, 2-1, and 2-2 (FIG. 1). All reactions are done using one cycle at 95° C. for 5 minutes, 45° C. for 1 minute and 72° C. for 2 minutes followed by 25 cycles at 95° C. for 1 minute, 45° C. for one minute and 72° C. for 2 minutes. Aliquots (10 µl) of the reactions were electrophoresed on an agarose gel, and in two of the reactions, one with primers 1-2 and 2-1 and one with primers 1-2 and 2-2, an amplification product of approximately 1100 bp is the major species. The predicted size of a product using these oligonucleotide combinations assuming there are no introns within the gene is 900 bp. the 1100 bp amplification product is subcloned and sequenced using the forward and reverse primers. Seven of the subclones are sequenced; however, none of them by homology code for CPY.

PCR reactions using various combinations of primers 3-1, 3-2, 4-1, 4-2, 2-1 and 2-2 are run using the same conditions as above. Aliquots are electrophoresed on an agarose gel, and in two of the reactions, one with primers 4-1 and 2-1 and one with primers 4-2 and 2-1, an amplification product of approximately 600 bp is the major species. The expected size for this amplification product based on homology to other carboxypeptidases is 600 bp. The 600 bp amplification product is subcloned and the DNA sequence is determined for 11 of the subclones using the forward and reverse primers. Nine of the 11 subclones, based on identity of 69% to *S. cerevisiae*, code for CPY from *A. niger*. All 9 are identical to one another suggesting there is only one gene for carboxypeptidase in *A. niger*. The subclone containing the *A. niger* CPY PCR product of 600 bp is designated pDSY17.

A Southern blot of *A. niger* Bo-1 genomic DNA is probed with the insert from pDSY17. The probe is radiolabeled using a nick-translation kit from Gibco-BRL. Hybridization conditions used are 60° C. in 1.5× SSPE, 1% SDS, 0.5% nonfat milk and 200 µg/ml salmon sperm DNA. The blot is washed at 65° C. for 15 minutes twice in 0.2× SSC, 1% SDS and 0.1% Na pyrophosphate. In the BamHI, HindIII and SAlI digests, single bands of approximately 10, 5.5 and 7 kb, respectively hybridize to the CPY probe.

In order to isolate the full gene for CPY, a genomic bank in EMBL4 of *A. niger* Bo-1 containing approximately 26,000 recombinants is probed with the PCR-derived CPY gene fragment, radiolabeled with the Gibco-BRL nick translation kit. Approximately 28,000 plaques are lifted to filters and probed. Eleven positives from these plates are picked. After purification, 9 of the primary clones still hybridized with the CPY probe. DNA is isolated from the 9 clones, and restriction digests are done in order to begin characterizing them. From the restriction patterns, 7 of the 9 are identical. The other two clones are unique. From Southern digests of the clones, it is determined that 8 of the 9 have the same HindIII fragment of approximately 5.5 kb which hybridizes to the CPY probe. The clone which does not contain the same HindIII fragment contains a larger (>12 kb) HindIII fragment which hybridizes to the CPY probe. The common HindIII fragment is subcloned for DNA sequencing. The genomic DNA sequence and predicted amino acid sequence is shown in FIG. 1.

A cDNA bank in Lambda ZAPII(Stratagene) of *A. niger* SFAG-2 is also screened. Approximately 42,000 plaques are lifted to filter and probed with the CPY probe as above, and 112 of these plaques appear to hybridize under the stringent conditions defined above. Twenty of the initial positives are picked and rescreened, and upon purification, 18 still hybridize with the CPY probe. From 4 of the positive clones, DNA is isolated using the in vivo excision protocol provided with the Lambda Zap kit. The rescued plasmids are digested with EcoRI and electrophoresed on an agarose gel to determine the sizes of the inserts. Two of the clones (2-1 and 3-2) appear to have large enough inserts to contain the full length cDNA for CPY, and each contains two EcoRI fragments of approximately 1700 and 250 bp. The predicted size for a full length cDNA is approximately 1600 bp. The other two cDNA clones (2-2 and 2-4) have smaller inserts; however, they all contain the 250 bp EcoRI fragment. Partial DNA sequences of clones 3-2 and 2-2 are determined, and 3-2 contains the full-length cDNA while clone 2-2 is truncated at the 5' end by about 200 bp.

The complete cDNA sequence is determined on both strands (FIG. 2). The cDNA is predicted to code for a CPY precursor of 557 amino acids in length. To date most of the nucleotide differences found between the cDNA and genomic clones are within the wobble which is not surprising since they come from two different *A. niger* strains. Based on an alignment with CPY from *S. cerevisiae*, CPY from *A. niger* appears to have both a signal peptide and a propeptide and the mature CPY protein is either 419 or 420 amino acids in length. *A. niger* CPY has approximately 65% and 66% identity to CPY from the yeasts *S. cerevisiae* and *C. albicans* (Mukhtar et al., Gene 121: 173–177, 1992), respectively.

II. PREPARATION OF A CPY-DEFICIENT MUTANT

In order to create an *A. niger* strain deleted for CPY, a construct in whichthe *A. oryzae* pyrG gene is inserted into the coding region of CPY is made (FIG. 3). An ~6.5 kb HindIII fragment containing almost the entire gene of CPY and ~6 kb downstream of the gene is subcloned into a pKS+(Stratagene) derivative in which the PstI site has been destroyed. The resulting recombinant is digested with PstI to delete an 815 bp fragment from the CPY coding region, and the overhangs created by digestion with PstI are blunted by the addition of T4 DNA polymerase and all 4 dNTPs. The resulting blunt-end vector is ligated to an ~3.8 kb blunt-end fragment obtained by digestion with HindIII followed by a fill-reaction using Klenow fragment. The final construct in which the CPY gene has the pyrG inserted is digested with HindIII to create a linear fragment which is used to transform an *A. niger* pyrG strain selecting for growth on minimal medium plates. Transformants are screened by Southern blotting to determine which strains contain a disrupted CPY gene. The transformants are further analyzed by Western blotting to look for the absence of CPY intracellularly. Once a strain is identified as containing a disruption of CPY, the effect on heterologous protein is determined.

Deposit of Biological Materials

The following biological materials have been deposited on Sep. 13, 1994 in Agricultural Research Service Culture Collection (NRRL) 1815 North University Street, Peoria, Ill. 61604.

| Cell line | Accession No. |
| --- | --- |
| *E. coli* containing pDSY23 (EMCC #0120) | NRRL B-21326 |

What is claimed is:

1. A method for producing a non-carboxypeptidase Y-producing filamentous ascomycete cell, comprising:
   (a) replacing the endogenous carboxypeptidase Y gene by homologous recombination with a nucleic acid sequence selected from the group consisting of (i) the nucleic acid sequence depicted in SEQ ID NO: 1 or SEQ ID NO: 3 and (ii) a nucleic acid sequence which hybridizes with SEQ ID NO: 1 or SEQ ID NO: 3 under high stringency conditions; which sequence is disrupted; and
   (b) obtaining from step (a) a cell which produces reduced amounts of carboxypeptidase Y relative to the amount produced by the wild-type strain.

2. The method of claim 1, wherein the nucleic acid sequence which has been disrupted is the nucleic acid sequence depicted in SEQ ID NO: 1.

3. The method of claim 1, wherein the nucleic acid sequence which has been disrupted is the nucleic acid sequence depicted in SEQ ID NO: 3.

4. The method of claim 1, wherein the nucleic acid sequence which has been disrupted is a nucleic acid sequence which hybridizes with SEQ ID NO: 1 under high stringency conditions.

5. The method of claim 1, wherein the nucleic acid sequence which has been disrupted is the nucleic acid sequence which hybridizes with SEQ ID NO: 3 under high stringency conditions.

6. The method of claim 1, wherein the nucleic acid sequence has been disrupted by insertion of a selectable marker.

7. The method of claim 6, wherein the selectable marker is amdS, pyrG, argB, niaD, sC, or hygB.

8. The method of claim 1 wherein the cell is selected from the group consisting of Aspergillus, Fusarium, Penicillium, Humicola, Trichoderma, Scytalidium, Myceliophthora and Thielavia.

9. The method of claim 8 which is *Aspergillus niger*.

* * * * *